United States Patent [19]

Spiro et al.

[11] Patent Number: 4,565,248

[45] Date of Patent: Jan. 21, 1986

[54] METHOD FOR PRODUCING WATER SOLUBLE RESOLS AND USE THEREFOR

[75] Inventors: Clifford L. Spiro, Schenectady; Edward J. Lamby, Scotia, both of N.Y.

[73] Assignee: General Electric Company, Schenectady, N.Y.

[21] Appl. No.: 633,750

[22] Filed: Jul. 24, 1984

Related U.S. Application Data

[62] Division of Ser. No. 446,134, Dec. 2, 1982, Pat. No. 4,499,311.

[51] Int. Cl.$^4$ ............ E21B 43/22; E21B 43/40
[52] U.S. Cl. .................... 166/267; 166/275; 166/371; 252/8.55 R; 252/8.55 D; 252/351; 528/660
[58] Field of Search ........... 166/263, 266, 267, 305 R, 166/306, 310, 312, 371; 252/8.55 R, 8.55 B, 8.55 D, 351; 568/660

[56] References Cited

U.S. PATENT DOCUMENTS

| | | | |
|---|---|---|---|
| 2,827,121 | 3/1958 | Nowak | 252/8.55 R X |
| 2,972,600 | 2/1961 | Braidwood | 568/660 X |
| 3,107,726 | 10/1963 | Greenwald | 166/266 |
| 3,467,195 | 9/1969 | McAuliffe et al. | 252/8.55 R |

OTHER PUBLICATIONS

Niederl et al., Journal of American Chemical Society; vol. 67, pp. 1176–1177 (1945).
Simon R. et al., "Down-Hole Emulsification for Improving Viscous Crude Production", *Journal of Petroleum Technology*, vol. XX, No. 12, Dec. 1968, pp. 1349–1353.

*Primary Examiner*—George A. Suchfield
*Attorney, Agent, or Firm*—George B. Fox; James C. Davis, Jr.; Bernard J. Lacomis

[57] ABSTRACT

The effluent stream from a process for producing phenolic compounds is reacted with an aldehyde in the presence of a base to form a water soluble resol which is useful in enhanced oil recovery.

27 Claims, No Drawings

METHOD FOR PRODUCING WATER SOLUBLE RESOLS AND USE THEREFOR

This application is a division of application Ser. No. 446,134, now U.S. Pat. No. 4,499,311, filed 12/2/82.

BACKGROUND OF THE INVENTION

This invention relates to a method for producing water soluble resols and use therefor. More particularly, it relates to a method for efficiently using pure phenolic compounds, blends of phenolic compounds and effluent streams of processes for producing phenolic compounds. Resols are the first stage of condensation of phenol-formaldehyde resins or alternatively a single stage synthetic resin produced from a phenol and an aldehyde.

In the production of bis(hydroxyaryl) compounds such as 4,4'-isopropylidene diphenol (bisphenol A or BPA), effluent streams of little commercial value are generated. Currently the materials of these effluent streams are burned for process heat. However, these materials have a relatively low heating value. It would be desirable to beneficially employ these materials in a manner in which a higher economic value can be realized.

Current primary methods such as pumping and secondary methods such as water-flooding for removing crude oil from oil wells leave a substantial portion of the available crude oil in the ground. It would be desirable to have a method for increasing the amount of crude oil recovered from these walls.

Accordingly, it is an object of the present invention to provide a method of using the effluent stream from a process for the production of bis(hydroxyaryl) compounds such that a greater economic value than currently realized may be obtained from the effluent stream.

Another object of the present invention is to provide a method of using resols based on pure phenolic compounds and blends of phenolic compounds.

A further object of the present invention is to provide an enhanced method for recovering crude oil from oil wells.

Still another object of the present invention is to provide a method of emulsifying in situ crude oil in oil wells.

SUMMARY OF THE INVENTION

In accordance with the present invention a method for producing water soluble resols comprises reacting the effluent stream of a process for producing BPA with an aldehyde in the presence of a compound for releasing hydroxide ions in water.

Further, a method for recovering crude oil comprises dissolving a water soluble resol made in accordance with the present invention in water, introducing the solution into oil wells in order to emulsify at least a portion of the crude oil contained therein, recovering the emulsion from the well and separating the crude oil from the emulsion.

The features of the invention believed to be novel are set forth with particularity in the appended claims. The invention itself, however, both as to organization and method of operation, together with further objects and advantages thereof, may best be understood by reference to the detailed description.

DETAILED DESCRIPTION

Currently employed processes for the manufacture of bis(hydroxyaryl) compounds, for instance bisphenols such as those disclosed in Faler et al.—U.S. Pat. Nos. 4,294,995 and 4,346,247, issued Oct. 13, 1981 and Aug. 24, 1982, respectively, and both being assigned to the instant assignee, generate effluent streams of little commercial value. The materials of these effluent streams currently are burned to produce process heat. However, the heating value of such materials is relatively insignificant.

In a process for the production of bisphenols such as is disclosed in Faler et al.—U.S. Pat. No. 4,365,099, assigned to the instant assignee and incorporated herein in its entirety by reference, the effluent stream may comprise bis(hydroxyaryl) or bisphenol compounds having the general formula:

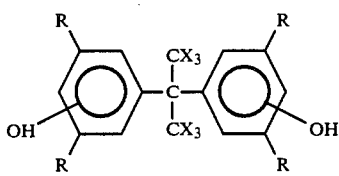

where each R is independently selected from the group consisting of hydrogen, monovalent alkyl (including aralkyl) groups of from 1 to 12 carbon atoms (e.g. methyl, ethyl, benzyl, propyl, isopropyl, hexyl, 2-ethylhexyl, etc.); aryl (e.g. phenyl, naphthyl, etc.); and alkaryl (e.g. tolyl, etc.); and each X is independently selected from the group consisting of hydrogen, fluorine, and alkyl radicals the same as R above (R and X can be the same or different as defined) and each hydroxyl radical is independently substituted on any one of the non-R substituted ring positions of its respective ring and further may comprise a phenolic compound having the general formula:

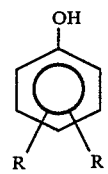

where R has the meaning given above and can be the same or different and each R is independently substituted on any non-hydroxyl substituted ring position.

By the term "phenolic compounds" as used herein and in the appended claims is meant those organic compounds containing an aromatic radical and one nuclearly bonded hydroxyl group. Phenolic compounds which can be used in the practice of the present invention are, for example, phenol and substituted phenols. Suitable phenolic compounds include phenol, xylenols, cresols, e.g. thymol, carvacrol, and cumenol, 2-methyl-6-ethylphenol, 2-ethyl-6-phenylphenol, 2-ethyl-6-methylphenol, 2-methyl-6-tertiary-butylphenol, 2,4-diethylphenol, 2,6-dimethylphenol, 2,6-ditertiary-butylphenol, o-phenylphenol, p-phenylphenol, p-ethylphenol, p-dodecylphenol, p-cresol, o-cresol, p-tert-butylphenol, o-tert-butylphenol, amylphenol blend, o-isopropylphenol, p-isopropylphenol, 6-hexadecyl-2- methylphenol, and the napthols, phenanthrol, and their homologues and analogues.

It has been found that the reaction of pure BPA phenolic compounds, mixtures of phenolic compounds, and effluent streams from processes for producing phenolic compounds such as PBA, with aldehydes, such as aliphatic aldehydes of from 1 to 12 carbon atoms, furfural and benzaldehyde, and a base or compound for releasing hydroxide ions in water such as sodium hydroxide, potassium hydroxide or ammonium hydroxide, yields a water soluble resol which is caustic stable. This reaction proceeds in water at ambient temperature although heating not to exceed 100° C. may facilitate the synthesis which is limited by the slow dissolution of the phenolic compounds in aqueous caustic.

The water soluble resols resulting from these reactions have been found to be effective surfactants for enhanced oil recovery (EOR). Current primary methods such as pumping and secondary methods such as waterflooding for removing crude oil from oil wells leave a substantial portion of the available crude oil in the ground. The crude oil production from these wells can be increased by mixing the resols produced by the methods of the present invention with the water or stream currently used for flooding the underground wells.

In order that those skilled in the art will be better able to understand and practice the invention, the following examples are given by way of illustration and not by way of limitation.

EXAMPLE I

In 250 ml. of water containing 50 g. sodium hydroxide, 100 g. of effluent from a BPA process stream was slurried. Two hundred fifty milliliters of 37% aqueous formaldehyde was added to the slurry. This reaction was carried out at room temperature between about 20° to about 25°C. Removal of excess water was accomplished by rotary evaporation leaving highly viscous resol oils. These resol oils tolerated highly caustic solutions and were quite water soluble. These resol oils were tested with aqueous suspensions of synthetic crude, naturally produced crude and refinery bottoms such as Bunker C fuel oils, the latter of which better resembles heavy crudes.

For comparison, an approximately 1% weight solution of dodecylammonium bromide (a surfactant) in water had no apparent visible effect on a droplet of Bunker C oil suspended in water. In contrast, less than a 0.1% aqueous solution of resol oils prepared in accordance with example I of the present invention emulsified the Bunker C oil almost instantly upon contact. The resol oils prepared in accordance with example I of the present invention also emulsified the synthetic crude and naturally produced crude oils.

EXAMPLE II

Fifty grams of sodium hydroxide was dissolved in 250 ml. of distilled water. Forty grams of bisphenol A was added as a solid, forming a slurry. Forty grams of cresol and 1.5 ml. of p-dodecylphenol were added neat. Fifty milliliters of a 37% solution of aqueous formaldehyde was subsequently added initially with stirring, followed by an additional increment of 50 ml. five minutes later. The resultant product was used without further purification.

EXAMPLE III

A resol of the type

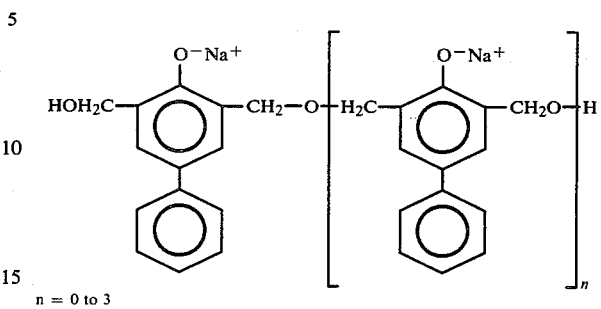

$n = 0$ to $3$ was made by reacting 34 gm. of p-phenylphenol with 32 gm. of 37% aqueous formaldehyde in the presence of 8.0 gm. of sodium hydroxide in 25 ml. of methanol and 100 ml. of water at 85°–90° C. over a 10-minute period to room temperature. The solution was held at 90° C. for 30 minutes before cooling.

To test for suitability as a surfacant for enhanced oil recovery, a Berea sandstone linear cores was utilized to model a reservoir. The core was initially saturated with brine followed by a saturation with natural crude oil until no brine was observed exiting the core. Brine was then continuously flushed through the oil saturated core until no increments of oil were observed exiting the core. Then a 1000 ppm solution of the resultant product of example I in water was continuously flushed through the core, resulting in an additional recovery of approximately 20% of the residual oil in the model reservoir.

Aqueous solutions of resols made in accordance with the present invention at a concentration of 10 ppm. (on a dry, waterfree basis) to saturation exhibit surfactant capabilities with respect to a variety of oils and hydrocarbons including pure hexane, iso-octane, a range of light to heavy crude oils and residual oil (Bunker C). Resols prepared from blends of phenols appear most effective in generating stable emulsions of crude oils. In general, resols prepared from phenols with highly aromatic subsitutents best emulsified the highly aromatic heavy crude and residual oils while resols prepared from phenols with highly aliphatic subsitutents best emulsified highly aliphatic crude oils and hydrocarbons. Since crude oils typically comprise blends of aromatic and aliphatic hydrocarbons, such a result is due to the non-homogeneous nature of the crude and residual oils and the variety and strength of the polarization of the resols available in a blend.

In operation, a blend of the resols made in accordance with the present invention would be dissolved in water in concentrations of from about 10 to about 1000 ppm., more preferably about 500 to about 1000 ppm. and most preferably about 600 ppm. The water having the water soluble resols dissolved therein would then be introduced into oil wells in order to emulsify a portion of the crude oil contained therein. The resulting aqueous mixture or emulsion containing crude oil would be recovered from the well and crude oil would be separated from the aqueous mixture by conventional means such as gravity, centrifuge or the addition of a de-emulsifying agent. Other uses of the surfactants (resols) of the present invention may also be wetting agents, industrial cleansers, coal slurries and in general where surface-active agents are used. It is estimated that the net heating value of a pound of effluent is less than about $0.10 based on the average Btu's per weignt whereas the net estimated value of a pound of surfactant is up to about $2.00.

Thus has been described a method for increasing the economic utility of the effluent stream of a process for making phenolic compounds and of a use of the material (resols) so generated. Further, a use for resols based on pure phenolic compounds and blends of phenolic compounds has been shown. An enhanced method for recovering crude oil from oil wells and a method of emulsifying in situ crude oil in oil wells have also been described.

While only certain preferred features of the invention have been described by way of illustration, many modifications and changes will occur to those skilled in the art. It is to be understood that the appended claims are intended to cover all such modifications and changes as fall within the true spirit and scope of the invention.

What is claimed is:

1. A method for recovering crude oil comprising:
   (a) reacting the effluent stream of a process for producing bisphenol-A with an aldehyde in the presence of a compound for releasing hydroxide ions in water at a temperature not to exceed 100° C.;
   (b) dissolving the product of step a in water;
   (c) introducing the solution produced in step b into an oil well in order to emulsify at least a portion of the crude oil contained therein; and
   (d) recovering the emulsion created in step c from the oil well.

2. The method of claim 1 further comprising separating least a portion of the crude oil from the emulsion.

3. The method of claim 1 wherein the product of step a is dissolved in water in a concentration of from about 10 to about 1000 ppm.

4. The method of claim 1 wherein the product of step a is dissolved in water in a concentration of from about 500 to about 1000 ppm.

5. The method of claim 1 wherein the product of step a is dissolved in water in a concentration of about 600 ppm.

6. The method of claim 1 wherein said effluent stream comprises a bis(hydroxyaryl) compound having the general formula:

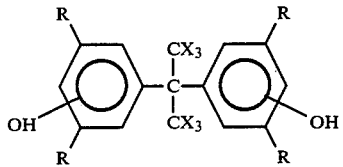

wherein each R is independently selected from the group consisting of hydrogen, monovalent alkyl (including aralkyl) groups of from 1 to 12 carbon atoms, aryl, and alkaryl and each X is independently selected from the group consisting of hydrogen, fluorine and alkyl radicals the same as R wherein R and X can be the same or different as defined and each hydroxyl radical is independently substituted on any one of the non-R substituted ring positions of its respective ring.

7. The method of claim 6 wherein said effluent stream further comprises a phenolic compound having the general formula:

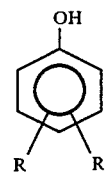

where R has the meaning given above and can be the same or different and each R is independently substituted on any non-hydroxyl substituted ring position.

8. The method of claim 7 wherein said phenolic compound is selected from the group consisting of phenols, cresols, xylenols, napthols and phenanthols.

9. The method of claim 8 wherein said phenolic compound is further selected from the group consisting of phenol, xylenol, thymol, carvacrol, cumenol, 2-methyl-6-ethylphenol, 2-ethyl-6-phenylphenol, 2,6-dimethylphenol, 2,6-ditertiary-butylphenol, o-phenylphenol, p-phenylphenol, p-ethylphenol, p-dodecylphenol, p-cresol, o-cresol, p-tert-butylphenol, o-tert-butylphenol, amylphenol blend, o-isopropylphenol, p-isopropylphenol, 6-hexadecyl-2-methylphenol.

10. The method of claim 1 wherein the aldehyde is selected from the group consisting of furfural, benzaldehyde and aliphatic aldehydes of from 1 to 12 carbon atoms.

11. The method of claim 1 wherein the compound for releasing hydroxide ions in water is selected from the group consisting of sodium hydroxide, potassium hydroxide and ammonium hydroxide.

12. The product produced by steps a and b of claim 1.

13. A method for recovering crude oil comprising:
   (a) selecting a compound from the group consisting of a bis(hydroxyaryl) compound having the general formula:

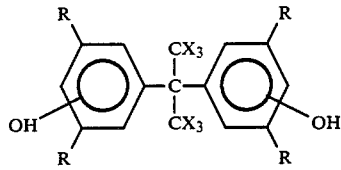

wherein each R is independently selected from the group consisting of hydrogen, monovalent alkyl (including aralkyl) groups of from 1 to 12 carbon atoms, aryl, and alkaryl and each X is independently selected from the group consisting of hydrogen, fluorine and alkyl radicals the same as R wherein R and X can be the same or different as defined and each hydroxyl radical is independently substituted on any one of the non-R substituted ring positions of its respective ring;
   (b) reacting said selected compound with an aldehyde in the presence of a compound for releasing hydroxide ions in water at a temperature not to exceed 100° C.;
   (c) dissolving the product of step b in water;
   (d) introducing the solution produced in step c into an oil well in order to emulsify at least a portion of the crude oil contained therein; and
   (e) recovering the emulsion created in step d from the oil well.

14. The method of claim 13 further comprising separating the at least a portion of the crude oil from the emulsion.

15. The method of claim 13 wherein the product of step a is dissolved in water in a concentration of from about 10 to about 1000 ppm.

16. The method of claim 13 wherein the product of step a is dissolved in water in a concentration of from about 500 to about 1000 ppm.

17. The method of claim 13 wherein the product of step a is dissolved in water in a concentration of about 600 ppm.

18. The method of claim 13 wherein the aldehyde is selected from the group consisting of furfural, benzaldehyde and aliphatic aldehydes of from 1 to 12 carbon atoms.

19. The method of claim 13 wherein the compound for releasing hydroxide ions in water is selected from the group consisting of sodium hydroxide, potassium hydroxide and ammonium hydroxide.

20. The product produced by steps a, b and c of claim 13.

21. A method for recovering crude oil comprising:
(a) selecting a phenolic compound having the general formula:

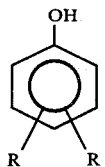

wherein each R is independently selected from the group consisting of hydrogen, monovalent alkyl (including aralkyl) groups of from 1 to 12 carbon atoms, aryl and alkaryl and each R can be the same or different;

(b) reacting said selected compound with an aldehyde in the presence of a compound for releasing hydroxide ions in water at a temperature not to exceed 100° C.;

(c) dissolving the produce of step b in water;

(d) introducing the solution produced in step c into an oil well in order to emulsify at least a portion of the crude oil contained therein; and (e) recovering the emulsion created in step c from the oil well.

22. The method of claim 21 further comprising separating the at least a portion of the crude oil from the emulsion.

23. The method of claim 21 wherein the product of step a is dissolved in water in a concentration of from about 10 to about 1000 ppm.

24. The method of claim 21 wherein the product of step a is dissolved in water in a concentration of from about 500 to about 1000 ppm.

25. The method of claim 21 wherein the produce of step a is dissolved in water in a concentration of about 600 ppm.

26. The method of claim 21 wherein the aldehyde is selected from the group consisting of furfural, benzaldehyde and aliphatic aldehydes of from 1 to 12 carbon atoms.

27. The method of claim 21 wherein the compound for releasing hydroxide ions in water is selected from the group consisting of sodium hydroxide, potassium hydroxide and ammonium hydroxide.

* * * * *